(12) United States Patent
McConnell et al.

(10) Patent No.: US 11,602,545 B2
(45) Date of Patent: Mar. 14, 2023

(54) HUMAN MILK OLIGOSACCHARIDES FOR TREATING MIGRAINE

(71) Applicant: Glycom A/S, Hørsholm (DK)

(72) Inventors: Bruce McConnell, La Tour de Peilz (CH); Louise Kristine Vigsnæs, Copenhagen (DK)

(73) Assignee: Glycom A/S, Hørsholm (DK)

( * ) Notice: Subject to any disclaimer, the term of this patent is extended or adjusted under 35 U.S.C. 154(b) by 344 days.

(21) Appl. No.: 16/770,336

(22) PCT Filed: Nov. 30, 2018

(86) PCT No.: PCT/IB2018/059503
§ 371 (c)(1),
(2) Date: Jun. 5, 2020

(87) PCT Pub. No.: WO2019/111115
PCT Pub. Date: Jun. 13, 2019

(65) Prior Publication Data
US 2020/0353005 A1  Nov. 12, 2020

(30) Foreign Application Priority Data
Dec. 5, 2017  (DK) .......................... PA 2017 00689

(51) Int. Cl.
*A61P 25/06* (2006.01)
*A61K 31/702* (2006.01)
*A61P 1/00* (2006.01)
*A61K 35/20* (2006.01)

(52) U.S. Cl.
CPC ............ *A61K 35/20* (2013.01); *A61K 31/702* (2013.01); *A61P 1/00* (2018.01); *A61P 25/06* (2018.01)

(58) Field of Classification Search
CPC ..................................................... A61K 31/702
USPC ............................................................ 514/61
See application file for complete search history.

(56) References Cited

FOREIGN PATENT DOCUMENTS

| WO | 2013126015 A1 | 8/2013 | |
|----|---------------|--------|---|
| WO | WO-2016066175 A1 * | 5/2016 | ............ A23C 9/206 |
| WO | 2017103019 A1 | 6/2017 | |
| WO | 2017198276 A1 | 11/2017 | |

OTHER PUBLICATIONS

Dobson, CF et al., Cephalalgia, "Effects of acute or chronic administration of anti-migraine drugs sumatriptan and zolmitriptan on serotonin synthesis in the rat brain", 2004, vol. 24, pp. 2-11 (Year: 2004).*
PCT/IB2018/059503, International Search Report, dated Jan. 30, 2019, pp. 1-8.
PCT/IB2018/059503, Written Opinion of the International Searching Authority, dated Jan. 30, 2019, pp. 1-10.
G. D'Andrea et al., "Tryptamine levels are low in plasma of chronic migraine and chronic tension-type headache", Neurol Sci. vol. 35, No. 12, Jul. 14, 2014, pp. 1941-1495.

* cited by examiner

*Primary Examiner* — Bahar Craigo
(74) *Attorney, Agent, or Firm* — Kunzler Bean & Adamson; Tom Briscoe

(57) ABSTRACT

The invention relates to a human milk oligosaccharide (HMO) for use in, a synthetic composition comprising an HMO for use in and a method for preventing or treating migraine in a human.

20 Claims, No Drawings

HUMAN MILK OLIGOSACCHARIDES FOR TREATING MIGRAINE

CROSS-REFERENCE TO RELATED APPLICATIONS

This application is a National Stage Entry under 35 U.S.C. § 371 of International Application PCT/IB2018/05950 filed on Nov. 30, 2018, which claims priority to Danish Patent Application No. PA 2017 00689 filed Dec. 5, 2017, the entirety of which are incorporated herein by reference.

FIELD OF THE INVENTION

This invention relates to a method, compounds and composition for the prevention and treatment of recurrent migraine in a human.

BACKGROUND OF THE INVENTION

Migraine headache is a common neurologic condition characterized by painful headaches associated with nausea, vomiting, and hypersensitivity to visual, auditory, and olfactory stimuli. Migraine attacks can cause significant pain for hours to days and can be so severe that the pain is disabling. Symptoms known as aura may occur before or with the headache. These can include flashes of light, blind spots, or tingling on one side of the face or in the arm or leg.

The worldwide prevalence of migraine headache is about 10%, however, it is slightly higher in the United States (about 12%). The Global Burden of Disease Study ranked migraine as the seventh most common disabling pathology among 289 diseases. Women experience migraine headache at a greater rate (1-17%) as compared to men. Migraine headache sufferers often experience substantial decreases in work productivity and function. This results in decreased quality of life for the patient and includes high financial burdens on individuals and employers. A conservative estimate of the migraine-related costs in the United States is estimated to be 78 billion dollars per year (Thompson et al. *J. Clin. Pharm. Ther.* 42, 394 (2017)).

Migraine is a neurovascular disorder involving cortical spreading depression, neurogenic inflammation, and dysfunction in cranial vascular contractility. Certain triggers can provoke a migraine attack. These include hormonal changes, emotional triggers, physical causes (like intense physical exertion), diet factors (e.g. alcohol, caffeine, nitrite), medication, and environmental triggers, e.g. bright light, strong smell or loud sound.

Despite intensive research, the exact pathomechanism of migraine is still not fully understood and complete preventive and attack therapy is still not available. It is believed that the fundamental mechanism of the migraine attack involves activation of the trigeminovascular system. Through a trigger mechanism, vasodilatation of the dural and pial blood vessels occurs, which can stimulate the perivascular trigeminal primary nerve endings. The activated nociceptors release neuropeptides at the periphery, including calcitonin generated peptide, substance P and neurokinin A. These substances cause inflammation of the trigeminal nerve. When the inflammation and blood vessels interact, the blood vessels dilate, leading to pain. The brain itself does not contain neurons that are sensitive to pain. Pain arises when pressure activates the nerves sensitive to pain in the tissues covering the brain or in the muscles and blood vessels around the face, neck and scalp.

Glutamate is the principal excitatory neurotransmitter in the central nervous system and plays an important role in primary afferent neurotransmission and nociception. Numerous human and animal studies suggest that glutamate and the glutamatergic system is overactive in migraine. Glutamate is an ionic form of the nonessential amino acid glutamic acid and it excites nearly every neuron contributing to primary neural transmission and pain perception. As a neurotransmitter, glutamate is synthesized from glutamine by the mitochondrial enzyme glutaminase and is stored in synaptic vesicles. During neurotransmission, it is released from the stores to the synaptic cleft and removed by the presynaptic glutamate transporter and the transporter located on the neighbouring glial cells.

Glutamate receptors are also found in the trigeminal system. One of the main glutamate ionotropic receptors is N-methyl D-aspartate (NMDA). Activation of NMDA by glutamate causes damage to cell structures and DNA causing neuronal cell death, and glutamate excitotoxicity is related to the hyperexcitability of NMDA receptors, which plays a key role in the pathophysiology of migraine. NMDA is activated or inhibited by metabolites of the kynurenine pathway.

Tryptophan is metabolized along the kynurenine and serotonin pathways, resulting in formation of kynurenine metabolites, and neuroactive serotonin and melatonin. The two pathways are unequal in their ability to degrade tryptophan with 95% of tryptophan catabolized by the kynurenine pathway and 5% catabolized by the serotonin pathways. In the kynurenine pathways, tryptophan is transformed to N-formyl-L-kynurenine by tryptophan 2,3-dioxygenase and indoleamine 2,3-dioxygenase (IDO), which are the rate-limiting enzymes of the Kynurenine pathway and are regulated by the cytokines TNF-α and IFN-γ. N-formyl-L-kynurenine can be further metabolized to L-kynurenine (L-KYN), which is the precursor of kynurenic acid (KYNA). L-KYN can also be degraded to anthranilic acid or to 3-hydroxy-L-kynurenine. Anthranilic acid and 3-hydroxy-L-kynurenine are then further transformed to 3-hydroxyanthranilic acid, which is metabolized to quinolinic acid. Among the Kynurenine pathway metabolites, many compounds are biologically active. 3-hydroxy-L-kynurenine and 3-hydroxyanthranilic acid are able to increase the formation of free radicals, yielding oxidative stress. On the contrary, KYNA has a neuroprotective function, since it acts as an antagonist for NMDA.

In the serotonin pathway, tryptophan is transformed to 5-Hydroxytryptophan by tryptophan hydroxylase. 5-Hydroxytryptophan can then be metabolized to serotonin, which can further be metabolized to melatonin by serotonin N-acetyl transferase. Melatonin has a very important role in tryptophan metabolism because it affects the two key enzymes of the two pathways; IDO and serotonin N-acetyl transferase. Melatonin has shown to induce the expression of IDO while decrease the expression of serotonin N-acetyl transferase.

Abnormalities of both the kynurenine and serotonin pathway have been reported in migraine suffers. Lower levels of serotonin and melatonin have been measured in patients with migraine compared to control, and a study has shown that chronic migraine patients had an astonishing elevation of anthranilic acid, with a decline in all other kynurenines especially KYNA. The reduction in the levels of KYNA can lead to overactivation of NMDA and low serotonin levels can lead to lower levels of melatonin, which again can cause an imbalance in the kynurenine metabolites. These events lead to migraine headaches. In addition, depletion of tryptophan has shown to increases nausea, headache and photophobia in migraine patients (Drummond Cephalalgia 26, 1225 (2006); Curto et al. J. Headache Pain 17:47 (2016)). This suggests that the level and catabolism of tryptophan is dysregulated in patients with migraine.

Since tryptophan is an essential amino acid with an estimated dietary requirement of 5 mg/kg/day and it is the limiting amino acid in nearly all protein sources, dietary sources of tryptophan may not be enough to obtain a regulated kynurenine and serotonin pathway. Therefore, there is a need for a safe, effective intervention for obtaining enough tryptophan for regulating these two pathways.

The level of essential vitamins such as riboflavin, folate and pyridoxal phosphate are also important for protecting against neurotoxicity. The three B-vitamins can act through ameliorating oxidative stress, mitochondrial dysfunction, neurogenic inflammation, and glutamate excitotoxicity, and they play a key role in the tryptophan-kynurenine pathway. Hence, B vitamin insufficiency can lead to significant neurological consequences. Taking into consideration the limited vitamin absorption and utilization in 10-15% of global population, long term vitamin insufficiency could contribute to the development of multiple neurological disorders such as migraine. Although B-vitamins are present as supplements, and in a variety of foods, deficiencies still occur, mainly due to low bioavailability, and malnutrition because of insufficient food intake and unbalanced diet. Vitamin B supplements have been used in the treatment of therapy for migraine, however, in situ fortification by intestinal bacteria seems to be a better option due to the constant bioavailability of the vitamins.

Increasing evidence suggests that the intestinal microbiota play a key role in the generation of neuroinflammatory disorders. The intestinal microbiota consists of a vast bacterial community that resides primarily in the colon and lives in a symbiotic relationship with the host. The human gastrointestinal microbiota includes at least 1000 different species of bacteria, which collectively make up to $10^{14}$ bacterial cells, tenfold the number of human cells, and they encode 100-fold more unique genes than the human genome (Qin et al. Nature 464, 59 (2010)). The intestinal bacteria may directly communicate with the central nervous system by way of the vagus sensory nerve. The vagus sensory nerve is a key component of the neuro-immune and brain-gut axes through a bidirectional communication between the brain and the gastrointestinal (GI) tract.

Significant associations have also been reported between migraine and a range of inflammatory disorders such as asthma, obesity, metabolic syndrome, allergies and GI disorders such as irritable bowel syndrome and celiac disease. These associations have been found in two directions: migraine patients have more often GI disorders compared with healthy controls, and patients with GI disorders more often suffer from migraine compared to control groups. This indicates a significant association between gut and migraine. This associations could be explained by an altered intestinal microbiota, an inflammatory immune response and an increased intestinal permeability, all of which have been found in GI disorders. An altered intestinal microbiota has been observed in migraine suffers, and people with GI disorders. This can cause an increase in the intestinal permeability. Impaired permeability allows leakage of indigestible food particles and bacterial components like liposaccharides (LPS) into the bloodstream. The present of LPS and detrimental metabolites in the blood stream can affect the blood-brain barrier. A disruption of the blood-brain barrier can lead to neuroinflammation and trigger a response provoking migraine (Lankarani et al. Middle East J. Dig. Dis. 9, 139 (2017)). In addition, gamma-aminobutyric acid (GABA) is a potent inhibitory neurotransmitter that can both be created and destroyed by intestinal bacteria. Hence, an imbalance in the metabolism of GABA could be linked to the occurrence and frequency of migraine attacks.

At present, there is no cure for migraine. Typically, pain is treated using pain-relieving medications such as aspirin, ibuprofen and triptans. Generally, these medications are either useful only for mild migraine or have significant side effects such as nausea, dizziness, drowsiness, muscle weakness, strokes and heart attacks. Preventative medication is available, but none of the currently available preventive means medication stops headaches completely and they have serious side effects. Usually, these medications have been developed for other purposes such anti-depressants, anti-seizure, etc.

WO 2017/198276 describes synthetic compositions and methods for the prophylaxis or treatment of serotonin and/or tryptophan dysregulation in a human using human milk oligosaccharides, particularly for improving gut motility. Conditions mentioned are depression, anxiety, anger, being unusually sensitive to pain, carbohydrate cravings and binge eating, constipation, digestive disorders, feeling glum from lack of sunlight, feeling overly dependent on others, feeling overwhelmed, hypervigilance, insomnia, joylessness, low self-esteem, migraines, poor cognitive function and tinnitus.

There are currently no interventions for prophylactically reducing episode occurrence or episode severity for recurrent migraine which are effective and have limited side effects. Therefore, there is a great need for methods and compounds for preventing or treating recurrent migraine in humans which are effective, safe and well tolerated.

SUMMARY OF THE INVENTION

A first aspect of the invention relates to a human milk oligosaccharide (HMO) for use in prophylactically reducing
   symptom severity of recurrent migraine and/or
   recurrence of migraine, especially the frequency of recurrence of migraine, in a human.

A second aspect of the invention relates to a synthetic composition for use in prophylactically reducing
   symptom severity of recurrent migraine and/or
   recurrence of migraine, especially the frequency of recurrence of migraine, in a human, the composition comprising at least one human milk oligosaccharide (HMO).

Preferably, the synthetic composition contains an amount of 1 g to 15 g of the HMO; more preferably 2 g to 10 g. For example, the synthetic composition may contain 3 g to 7 g of the HMO.

The synthetic composition may contain a bifidobacteria, for example *Bifidobacterium longum* and/or *Bifidobacterium bifidum*. The synthetic composition may also comprise a source of magnesium, a vitamin B source, melatonin, coenzyme Q10 and/or an omega-3 long-chain fatty acid.

A third aspect of the invention relates to a method for prophylactically reducing symptom severity of recurrent migraine in a human, the method comprising administering to the human an effective amount of at least one human milk oligosaccharide (HMO).

A fourth aspect of the invention relates to a method for prophylactically reducing recurrence of migraine, especially the frequency of recurrence of migraine, in a human, the method comprising administering to the human an effective amount of at least one human milk oligosaccharide (HMO).

The human may suffer from chronic migraine and/or may have another disorder, e.g. an inflammatory disorder (such as asthma), obesity, metabolic syndrome, allergies and GI disorders (such as irritable bowel syndrome and celiac disease). The another disorder is not abnormal serotonin or tryptophan metabolism.

Preferably, the human is administered the HMO for a period of at least 1-2 weeks, more preferably for at least 3 to 4 weeks, e.g. 2-4 months, 5-12 months, or longer. In one embodiment, the treatment may be temporarily discontinued and resumed again, if the patient experiences the incidence of migraine following discontinuation of the HMO intake. In other embodiment, the treatment may be permanently discontinued, if the patient does not have incidences of migraine for a long period of time, e.g. 3-6 months, after the discontinuation.

A fifth aspect of the invention relates to a method for prophylactically reducing
the average number of headache days in a chronic migraine patient, or
the severity of a migraine symptoms in a chronic migraine patient, the method comprising administering to the patient an effective amount of at least one human milk oligosaccharide for a period of at least 14 days.

Preferably, the human is administered an amount of 1 g to 15 g per day of the HMO, more preferably 2 g to 10 g per day. For example, the human may be administered 3 g to 7 g per day. The human may be administered higher doses during an initial phase and lower doses during a second, maintenance phase.

A sixth aspect of the invention is a pack for use in prophylactically reducing
symptom severity of recurrent migraine and/or
recurrence of migraine, especially the frequency of recurrence of migraine, in a human, the pack comprising at least 14 individual daily doses of an effective amount of at least one human milk oligosaccharide (HMO).

Preferably, each dose in the pack contains about 1 g to 15 g of the human milk oligosaccharide, preferably 2 g to 10 g, more preferably 3 g to 7 g. Further, the pack preferably comprises at least about 21 daily doses, for example about 28 daily doses.

The daily doses, in addition to the amount of an HMO mentioned above, may comprise a source of magnesium, a vitamin B source, melatonin, coenzyme Q10, an omega-3 long-chain fatty acid and/or choline. Alternatively, the pack may additionally comprise at least 14 daily doses of a source of magnesium, a vitamin B source, melatonin, coenzyme Q10, an omega-3 long-chain fatty acid and/or choline.

The HMO can be a neutral HMO or an acidic HMO. The neutral HMO can be one or more fucosylated HMOs or one or more non-fucosylated HMOs. Preferably, the HMO is selected from 2'-FL, 3-FL, DFL, LNT, LNnT, 3'-SL, 6'-SL, LNFP-I or a mixture thereof. Preferably, the HMO comprises, consists of or essentially consists of 2'-FL and at least one of LNnT and LNT; at least one of 2'-FL and DFL and at least one of LNnT and LNT (e.g. 2'-FL, DFL and at least one of LNnT and LNT); 2'-FL and 6'-SL; DFL and 6'-SL; 2'-FL, DFL and 6'-SL; 2'-FL, 6'-SL and at least one of LNnT and LNT; and 2'-FL, DFL, 6'-SL and at least one of LNnT and LNT. The human can suffer from a disease or condition involving gastrointestinal symptoms.

For example, the disease or condition can be an autoimmune disease such as coeliac disease, irritable bowel syndrome, an allergy and/or a food intolerance such as non-coeliac gluten/wheat intolerance.

Preferably, the human is a non-infant human.

The human may be further administered a source of magnesium, a vitamin B source, melatonin, coenzyme Q10, an omega-3 long-chain fatty acid, choline and/or a probiotic bacterium, e.g. one or more bifidobacterial species. Preferably, the human is further administered a vitamin B source, an omega-3 long-chain fatty acid and/or choline.

A sixth aspect of the invention relates to a method of dietary management of a chronic migraine patient, the method comprising administering to the patient an effective amount of at least one human milk oligosaccharide for a period of at least 14 days.

DETAILED DESCRIPTION OF THE INVENTION

Human milk oligosaccharides (HMOs) are a heterogeneous mixture of soluble glycans found in human milk. They are the third most abundant solid component after lactose and lipids in human milk and are present in concentrations of 5-25 g/l (Bode: *Human milk oligosaccharides and their beneficial effects*, in: Handbook of dietary and nutritional aspects of human breast milk (Zibadi et al., eds.), pp. 515-31, Wageningen Academic Publishers (2013)). HMOs are resistant to enzymatic hydrolysis in the small intestine and are thus largely undigested and unabsorbed and reach the colon intact. The majority of HMOs that reach the colon serve as substrates to shape the gut ecosystem by selectively stimulating the growth of specific bacteria. HMOs are believed to substantially modulate the infant gut microbiota and play a decisive role in the differences in the microbiota of formula-fed and breast-fed infants.

HMOs can preferentially increase the abundance of bifidobacteria in the gastrointestinal tract, in particular bifidobacteria of the *B. adolescentis* phylogenetic group, e.g. *Bifidobacterium longum* and/or *Bifidobacterium bifidum*. Bifidobacteria are able to synthesise B-vitamins such as riboflavin and folate de novo, ensuring its constant bioavailability, and can secrete neuromodulators such as GABA. In addition, species of bifidobacteria are able to synthesize tryptophan, and can impact immune regulation and expression of different immune markers such as IFN-$\gamma$ and TNF-$\alpha$. The kynurenine pathway is regulated by IFN-$\gamma$ and TNF-$\alpha$, hence selective stimulation of bifidobacteria can affect tryptophan metabolism and help regulate the serotonin and kynurenine pathways. Furthermore, fucosylated HMOs can stimulate the central nervous system through the afferent vagus nerve (Vazquez et al. *PLoS ONE* 11: e0166070 (2016)).

It has now been surprisingly found that oral or enteral administration of one or more HMOs to humans suffering from recurrent migraine reduces or prevents occurrence and/or reoccurrence of migraines in humans. Further, the severity and/or the frequency of migraine symptoms is reduced when these symptoms reoccur. The reduction occurs in humans that do not have gastrointestinal disorders and humans that suffer from gastrointestinal symptoms. Accordingly, the invention provides human milk oligosaccharides and synthetic compositions comprising thereof that may be used as a dietary primary and/or secondary prevention of recurrent migraine in humans.

In addition, administration of human milk oligosaccharides to humans, preferably non-infant children and adults, preferentially creates a beneficial intestinal microbiota. As an outcome, the gastrointestinal permeability and inflammation is diminished.

In this specification, the following terms have the following meanings that are applicable to all embodiments described herein, unless specified otherwise:

"Non-infant human" or "non-infant" means a human of 3 years of age and older. A non-infant human can be a child, a teenager, an adult or an elderly person.

"Human milk oligosaccharide" or "HMO" means a complex carbohydrate found in human breast milk (Urashima et al.: Milk Oligosaccharides. Nova Science Publisher (2011); Chen Adv. Carbohydr. Chem. Biochem. 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyl-lactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose 11 (LNFP-II), lacto-N-fucopentaose III (LNFP-III), lacto-N-difucohexaose III (LNDFH-III), fucosyl-lacto-N-hexaose 11 (FLNH-II), lacto-N-fucopentaose V (LNFP-V), lacto-N-fucopentaose VI (LNFP-VI), lacto-N-difucohexaose 11 (LNDFH-II), fucosyl-lacto-N-hexaose 1 (FLNH-I), fucosyl-para-lacto-N-hexaose 1 (FpLNH-I), fucosyl-para-lacto-N-neohexaose 11 (F-pLNnH 11) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose 1 (SLNH-1), sialyl-lacto-N-neohexaose 11 (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments, a synthetic composition may be, but preferably is not, identical with a naturally occurring composition. The synthetic composition typically comprises one or more compounds, including one or more HMOs, that are capable of preventing or treating migraine in a human. Also, in some embodiments, the synthetic compositions may comprise one or more nutritionally or pharmaceutically active components which do not affect adversely the efficacy of the above-mentioned compounds. Some non-limiting embodiments of a synthetic composition of the invention are also described below.

"Migraine" means a condition marked by recurring moderate to severe headache with throbbing pain that usually lasts from two hours to three days. It may have an early symptom (prodrome) indicating the onset of a disease or illness, e.g. constipation, mood changes food cravings, etc. The migraine attack typically begins on one side of the head but may spread to both sides and is often accompanied by nausea, vomiting and sensitivity to light or sound, and is sometimes preceded by an aura. It is often followed by one or more symptoms that occurs after the attack (postdrome) and last from a few hours to about 2-3 days, e.g, fatigue, mental confusion, skin and scalp sensitivity, mood change, etc. A "migraine patient" in the present context means an individual that suffers from the recurrent migraine headache attacks, either or not accompanied with prodrome and/or postdrome symptoms. "Reducing severity of migraine" means reducing one or more of the following symptoms: moderate to severe pulsating headache pain that is felt on one or both sides of the head, nausea, confusion, blurred vision, mood changes, fatigue, and increased sensitivity to light, sound, or smells that comes with the headache pain.

"Recurrent migraine" means that symptoms of migraine are experienced by the individual periodically, such one from once a week, once in two weeks, once a month or more seldom, with a migraine condition that lasts from about 2 hours to about 72 hours. "Frequency of recurrence" means the number of recurrent migraine episodes in a human in a period of time, e.g. during 1 month, 3 months, etc. According to the invention, the compositions disclosed herein and the methods of treatment reduce the frequency of recurrence of migraine in a chronic migraine patient by at least 25%, such as 30-50%.

"Chronic migraine" means a migraine condition in which the patient has at least 10 days with headache per month for at least 3 consecutive months. Chronic migraine is a more extreme version of recurrent migraine.

"Patient" in general is an individual suffering from a disease or a pathological condition who is currently or have been in the past put under observation or control by a qualified medical professional.

"Therapy" means treatment given or action taken to reduce or eliminate symptoms of a disease or pathological condition.

"Treat" means to address a medical condition or disease with the objective of improving or stabilising an outcome in the person being treated or addressing an underlying nutritional need. Treat, therefore, includes the dietary or nutritional management of the medical condition or disease by addressing nutritional needs of the person being treated. "Treating" and "treatment" have grammatically corresponding meanings.

"Preventive treatment" or "prevention" means treatment given or action taken to diminish the risk of onset or recurrence of a disease. The term "prophylactic treatment" is used herein interchangeably with the term "preventive treatment".

"Primary prevention" means prevention of onset of the condition in an individual who is not known to suffer from the condition.

"Secondary prevention" means prevention of onset of the condition in a high-risk individual, or prevention of reoccurrence of symptoms in a patient who has already has the condition. "High-risk individual" in the present context means an individual who is not known to suffer from the condition, e.g. migraine, but who is genetically predisposed or who has another physiological condition, e.g. a disease or metabolic disorder, such as an inflammatory disorder e.g. asthma, obesity, metabolic syndrome; allergies; GI disorders such as irritable bowel syndrome or celiac disease, that can evoke the onset of the condition, e.g. a migraine attack.

"Reducing migraine" means eliminating or diminishing at least one symptom associated with the migraine headache in an individual, preferably two or more symptoms, preferably all symptoms of migraine in the individual. "Preventing migraine" means reducing the risk of occurrence or recurrence of one or more symptoms associated with migraine, preferable two or more symptoms, more preferably all symptoms of migraine in an individual. "Symptoms of migraine" preferably means a headache characterised by at least one of the following:

pain on one side or both sides of the head;
pain that feels throbbing or pulsing;
sensitivity to light, sounds, and sometimes smells and touch;
nausea and vomiting;
blurred vision;
light-headedness, sometimes followed by fainting.

"Severe migraine" means a migraine accompanied by at least one of the following symptoms: nausea, confusion, blurred vision, light-headedness, and sometimes followed by fainting, mood changes, fatigue, increased sensitivity to light, sound or smell, any of which may be accompanied by moderate to severe throbbing or pulsating headache that is felt on one or both sides of the head and occurs without warning.

The terms reducing and preventing migraine, in the present content, also relate to the prodrome and postdrome migraine symptoms. Other described symptoms of migraine (see e.g. on https://migraine.com/migraine-symptoms/) are also contemplated.

"Microbiota", "microflora" and "microbiome" mean a community of living microorganisms that typically inhabits a bodily organ or part, particularly the gastro-intestinal organs of humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria*, and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

"Enteral administration" means any conventional form for delivery of a composition to a human that causes the deposition of the composition in the gastrointestinal tract (including the stomach). Methods of enteral administration include feeding through a naso-gastric tube or jejunum tube, oral, sublingual and rectal.

"Oral administration" means any conventional form for the delivery of a composition to a human through the mouth. Accordingly, oral administration is a form of enteral administration.

"Effective amount" means an amount of an HMO sufficient to render a desired outcome in a human, in particular an amount of an HMO effective to reduce the severity of migraine symptoms or the incidence of recurrence of migraine in a chronic migraine patient. An effective amount can be administered in one or more doses to achieve the desired outcome. According to the invention, all and every value mentioned herein with regard to amounts of substances or days of treatment may deviate +/−10% without consequences to the treatment. This is indicated by the term "about".

"*Bifidobacterium* of the *B. adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13:S4 (2014)). Preferably, a *Bifidobacterium* of the *B. adolescentis* phylogenetic group is *Bifidobacterium adolescentis* and/or *Bifidobacterium pseudocatenulatum*.

"Modulating of microbiota" means exerting a modifying or controlling influence on microbiota, for example an influence leading to an increase in the indigenous intestinal abundance of *Bifidobacterium, Barnesiella* and/or *Faecalibacterium* and/or other butyrate producing bacteria. In another example, the influence may lead to a reduction of the intestinal abundance of *Ruminococcus gnavus* and/or Proteobacteria. "Proteobacteria" are a phylum of Gram-negative bacteria and include a wide variety of pathogenic bacteria, such as *Escherichia, Salmonella, Vibrio, Helicobacter, Yersinia* and many other notable genera.

"Dietary management" means exclusive or partial feeding of patients who, because of a disease, disorder or medical condition are suffering from:

either have a limited, impaired or disturbed capacity to take, digest, absorb, metabolise or excrete ordinary food or certain nutrients contained therein, or metabolites, or have other medically-determined nutrient requirements (see: Commission Notice on the classification of Food for Special Medical Purposes of the European Commission, *Official Journal of the European Union* C 401, 25 Nov. 2017, p. 10-11).

In accordance with this invention, the incidence and intensity of recurrent migraine in a human may be reduced or prevented by administering one or more HMOs to the human. The HMOs may be administered as individual compounds or in the form of a synthetic composition.

Accordingly, one aspect of the invention relates to a human milk oligosaccharide (HMO) for use in prophylactically reducing symptom severity of recurrent migraine and/or
recurrence of migraine, especially the frequency of recurrence of migraine, in a human.

Another aspect of this invention is a synthetic composition comprising an HMO for use in prophylactically reducing symptom severity of recurrent migraine and/or
recurrence of migraine, especially the frequency of recurrence of migraine, in a human.

Yet another aspect of this invention is a method for prophylactically reducing symptom severity of recurrent migraine in a human, the method comprising administering to the human an effective amount of at least one human milk oligosaccharide.

Yet another aspect of this invention is a method for prophylactically reducing recurrence of migraine, especially the frequency of recurrence of migraine, in a human, the method comprising administering to the human an effective amount of at least one human milk oligosaccharide.

Yet another aspect of this invention is a method for prophylactically reducing the average number of headache days in a chronic migraine patient, or
the severity of migraine symptoms in a chronic migraine patient the method comprising administering to the patient an effective amount of at least one human milk oligosaccharide for a period of at least 14 days.

Yet another aspect of this invention is a method for dietary management of a chronic migraine patient or a patient having recurrent migraine, the method comprising administering to the patient an effective amount of at least one human milk oligosaccharide for a period of at least 14 days.

Yet another aspect of this invention relates to a pack comprising at least 14 individual daily doses of an effective amount of at least one human milk oligosaccharide (HMO) for use in
- prophylactically reducing symptom severity of recurrent migraine and/or
- recurrence of migraine, especially the frequency of recurrence of migraine, in a human.

Yet another aspect of the invention is a use of
- one or more human milk oligosaccharides (HMOs),
- a synthetic composition comprising one or more human milk oligosaccharides (HMOs), or
- a pack comprising at least 14 individual daily doses of an effective amount of one or more human milk oligosaccharides in the dietary management of a patient suffering from recurrent or chronic migraine.

Concerning each aspect, the HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies.

As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. Descriptions of biotechnological methods to make core human milk oligosaccharides, optionally substituted by fucose or sialic acid, using genetically modified E. coli. can be found in WO 01/04341 and WO 2007/101862.

The HMO, in any of the above aspects, may be a single HMO or a mixture of any HMOs suitable for the purpose of the invention. The HMO can be a neutral HMO or an acidic HMO. The neutral HMO is, in one embodiment, one or more fucosylated HMOs; in another embodiment, the neutral HMO is one or more non-fucosylated HMOs. Particularly, the fucosylated neutral HMO is selected from the list consisting of 2'-FL, 3-FL, DFL, LNFP-I, LNFP-II, LNFP-III, LNFP-V, LNFP-VI, LNDFH-I, LNDFH-II, LNDFH-III, FLNH-I, FLNH-II, FLNnH, FpLNH-I and F-pLNnH II, preferably, 2'-FL, and the non-fucosylated neutral HMO is selected from the list consisting of LNT, LNnT, LNH, LNnH, pLNH and pLNnH, e.g. LNnT. The one or more fucosylated HMOs can be e.g. a mixture containing, consisting or consisting essentially of 2'-FL and DFL.

In one embodiment, the mixture comprises, consists of or essentially consists of, neutral HMOs, preferably at least a first neutral HMO and at least a second neutral HMO, wherein the first neutral HMO is a fucosylated neutral HMO and the second neutral HMO is a non-fucosylated neutral HMO. The fucosylated neutral HMO(s) and the non-fucosylated neutral HMO(s) may be present in a mass ratio of about 4:1 to 1:1. Particularly, the mixture of HMOs comprises, consists of or essentially consists of a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated neutral HMO selected from the list consisting of LNT, LNnT, LNH, LNnH, pLNH and pLNnH. More preferably, the mixture of neutral HMOs contains, consists of or essentially consists of, a fucosylated HMO selected from the list consisting of 2'-FL, 3-FL and DFL, and a non-fucosylated neutral HMO selected from the list consisting of LNT and LNnT; advantageously the mixture comprises, consists of or essentially consists of, 2'-FL and at least one of LNnT and LNT; or at least one of 2'-FL and DFL and at least one of LNnT and LNT; or 2'-FL, DFL and at least one of LNnT and LNT.

In other embodiment, the mixture comprises, consists of or essentially consists of, at least a first (acidic) HMO and at least a second (neutral) HMO, wherein the first (acidic) HMO is selected from the list consisting of 3'-SL, 6'-SL and FSL and the second (neutral) HMO is selected from the list consisting of 2'-FL, 3-FL, DFL, LNT and LNnT; advantageously the mixture comprises, consists of or essentially consists of, 2'-FL and 6'-SL; or 6'-SL and at least one of 2'-FL and DFL; or 2'-FL, 6'-SL and at least one of LNnT and LNT; or 2'-FL, DFL, 6'-SL and at least one of LNnT and/or LNT.

In one embodiment, the synthetic composition can be in the form of a nutritional composition. For example, the nutritional composition can be a food composition, a rehydration solution, a medical food or food for special medical purposes, a nutritional supplement and the like. The nutritional composition can contain sources of protein, lipids and/or digestible carbohydrates and can be in powdered or liquid forms. The composition can be designed to be the sole source of nutrition or as a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for humans with inflamed or compromised GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve intestinal barrier function and mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from added lactose. Generally digestible carbohydrates provide about 35% to about 55% of the energy of the nutritional composition. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for humans with inflamed or compromised GI tracts. Generally, the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-3 (n-3) to omega-3 (n-6) ratio of about 4:1 to about 10:1. For example, the n-3 to n-6 fatty acid ratio can be about 6:1 to about 9:1. The polyunsaturated fatty acid may consist of an omega-3 fatty acid.

The nutritional composition may also include vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron. A source of magnesium, for example magnesium dicitrate (600 mg), may reduce migraine occurrence and intensity. The nutritional composition may also include coenzyme Q10. The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 µg/ml of lutein. Lycopene can be included in an amount from about 0.001 µg/ml to about 10 µg/ml, preferably about 0.0185 µg/ml to about 5 µg/ml of lycopene. Beta-carotene can comprise from about 0.001 µg/ml to about 10 mg/ml, for example about 0.034 µg/ml to about 5 µg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HNO19, *B. lactis* Bi07, *B. lactis* W52, *B. infantis* ATCC 15697, *B. bifidum*, *L. rhamnosus* GG, *L. rhamnosus* HNOOI, *L. acidophilus* LA-5, *L. acidophilus* NCFM, *L. brevis* W63, *L. casei* W56, *L. salivarius* W24, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be formulated as a soluble powder, a liquid concentrate, or a ready-to-use formulation. The composition can be fed to a human in need via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, it may be preferred that the total concentration of HMOs in the liquid, by weight of the liquid, is from about 0.1% to about 1.5%, including from about 0.21% to about 1.0%, for example from about 0.3% to about 0.7%. When the nutritional product is a concentrated nutritional liquid, it may be preferred that the total concentration of HMOs in the liquid, by weight of the liquid, is from about 0.2% to about 3.0%, including from about 0.4% to about 2.0%, For example from about 0.6% to about 1.5%.

In another embodiment, the nutritional composition is in a unit dosage form. The unit dosage form can contain an acceptable food-grade carrier, e.g. phosphate buffered saline solution, mixtures of ethanol in water, water and emulsions such as an oil/water or water/oil emulsion, as well as various wetting agents or excipients. The unit dosage form can also contain other materials that do not produce an adverse, allergic or otherwise unwanted reaction when administered to a human. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents.

A unit dosage form can be administered orally, e.g. as a tablet, capsule, or pellet containing a predetermined amount of the mixture, or as a powder or granules containing a predetermined concentration of the mixture or a gel, paste, solution, suspension, emulsion, syrup, bolus, electuary, or slurry, in an aqueous or non-aqueous liquid, containing a predetermined concentration of the mixture. An orally administered composition can include one or more binders, lubricants, inert diluents, flavouring agents, and humectants. An orally administered composition such as a tablet can optionally be coated and can be formulated to provide sustained, delayed or controlled release of the HMO.

The unit dosage form can also be administered by nasogastric tube or direct infusion into the GI tract or stomach.

The unit dosage form can also include therapeutic agents such as antibiotics, probiotics, a source of magnesium, melatonin, coenzyme Q10, omega-3 polyunsaturated fatty acids, analgesics, and anti-inflammatory agents. The proper dosage of such a composition for a human can be determined in a conventional manner, based upon factors such as the human's condition, immune status, body weight and age. In some cases, the dosage will be at a concentration similar to that found for the HMOs of the composition in human breast milk. The required amount would generally be in the range from about 1 g to about 15 g per day, in certain embodiments from about 2 g to about 10 g per day, for example about 3 g to about 7 g per day. Appropriate dose regimes can be determined by methods known to those skilled in the art.

In further embodiment, the HMO can be comprised in a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antibiotics, probiotics, analgesics, and anti-inflammatory agents. The proper dosage of these compositions for a human can be determined in a conventional manner, based upon factors such condition, immune status, body weight and age. In some cases, the dosage will be at a concentration similar to that found for the HMOs in human breast milk. The required amount would generally be in the range from about 1 g to about 15 g per day, in certain embodiments from about 2 g to about 10 g per day, for example from about 3 g to about 7 g or from about 4 g to about 8 g per day. Appropriate dose regimes can be determined by conventional methods.

For preventing or treating recurrent migraine in a human, the amount of HMO(s) required to be administered will vary depending upon factors such as the risk and severity of the recurrent migraine, any underlying medical condition or disease, age, the form of the composition, and other medications being administered. However, the required amount can be readily set by a medical practitioner and would generally be in the range from about 1 g to about 15 g per day, in certain embodiments from about 2 g to about 10 g per day, for example from about 3 g to about 7 g or from about 4 g to 8 g per day. An appropriate dose can be determined based on several factors, including, for example, body weight and/or condition, the severity of the recurrent migraine being treated or prevented, other ailments and/or diseases, the incidence and/or severity of side effects and the manner of administration. Appropriate dose ranges may be determined by methods known to those skilled in the art. In one embodiment, the method comprises a first and a second treatment phase. During the first (initial) phase, the dosing can be higher (for example about 3 g to about 15 g per day, preferably about 3 g to about 10 g per day). During the second (maintenance) phase, the dosing can be reduced (for example, about 1 g to about 10 g per day, preferably about 2 g to about 7.5 g per day).

EXAMPLES

Example 1

Patients of age between 18-70 years who have a history of recurrent migraine (according to the criteria of the International Classification of Headache Disorders, 3rd edition [beta version]) for at least 12 months are recruited. Patients fulfil the criteria for chronic migraine during the 28-day screening period (headache of any duration or severity on days and headache meeting ICHD-3 beta criteria for migraine on days). Key exclusion criteria are the use of preventative medication during the 4 months before screening; the use of preventative devices such as transcranial magnetic stimulation during the 2 months before screening; and the use of opioid or barbiturate medications on more than 4 days during the screening period. Patients are also excluded if pregnant or breast-feeding women.

At an initial visit (screening), each patient is given both written and oral information about the study and the patient is asked to sign an informed consent form. Each patient is evaluated by a full review of clinical history including headache/migraine history and undergoes a physical examination and a 12-lead electrocardiogram. Blood and urine samples are collected. Equipment for faecal sampling is distributed to each patient. Patients are instructed to keep their samples in the freezer until the next visit. Patients are provided with access to an electronic diary to record headache/migraine occurrence and intensity. A 4-point Likert scale is used for pain intensity where a score of "0" implies "no pain" and a score of "3" implies "severe pain". Patients also record associated migraine symptoms (e.g. nausea, photophobia and phonophobia), any medications used.

At a second visit (beginning of intervention) within 28 days of the first visit, eligibility criteria are checked, and eligible subjects are randomised to one of two arms. A total of 40 patients are included. Each arm has 20 patients, with one arm consuming the treatment product and one group the placebo product. The treatment product contains 5 grams of a combination of 2'-FL and LNnT while the placebo product contains 5 grams glucose. Both products are in powder form in a unit dosage container. The diary is reviewed, and an assessment is made of symptoms of physical and mental health, gastrointestinal symptoms, quality of life, and faecal consistency (as measured by SF36, GSRS, BSFS and QoL questionnaires). Trial supplementation is distributed along with instructions on use rescue medication. The faecal samples are collected and equipment for collecting new samples is distributed. Patients are instructed to maintain their current diet.

Blood samples and urine are collected for biomarker and biobanking. The serum from the blood samples is transferred to cryotubes and stored at −80° C. The following biomarkers are measured IFN-γ, TNF-α, IL-1β, IL-8, IL-6, IL-12, IL-10, MIP-1β, hs-CRP, lipopolysaccharide binding protein, fatty acid binding protein 2, tryptase, antiflagellin, zonulin, histamine, prostaglandin 2, and cortisol. To analysis the level of metabolites of the kynurenine and serotonin pathways following compounds were measured in serum; tryptophan, L-kynurenine, kynureninic acid and serotonin. Flow cytometry are performed on blood to determine the level of immune cells.

Urine samples are stored at −80° C. Bacterial metabolites such as SOFA were analysed in urine samples using NMR. The faecal samples are stored at −80° C. until analysis. Microbiological analysis is performed on the faecal samples using the 16S rRNA gene sequence.

At a third visit after 4 weeks, the faecal samples are collected, blood and urine samples are collected, and an assessment is made of headache/migraine occurrence and intensity, and of symptoms of physical and mental health, gastrointestinal symptoms, quality of life, and faecal consistency (as measured by SF36, GSRS, BSFS and QoL questionnaires). Trial supplementation and equipment for collecting new samples is distributed.

At the end of the intervention (week 8), each patient has a visit with the medical team. A physical examination is done and symptoms (as measured by the diary, GSRS, IBS-SSS, BSFS and QoL scales etc.) are reassessed. Trial supplementation products are collected to check compliance. Faecal samples and blood samples are collected and analysed as before.

The primary end point is the mean change in the average number of headache days (days in which headache pain lasted consecutive hours and had a peak severity of at least a moderate level or days in which acute migraine-specific medication [triptans or ergots] was used to treat a headache of any severity or duration) per month, comparing to the baseline 28-day screening period. The patients receiving the treatment product report a reduction in average number of headache days as compared to the placebo group. Further, where headache/migraine occurred, intensity is less in the treatment group. The treatment group also indicate improved gastrointestinal symptoms as determined by GSRS score and an improvement in faecal consistency as compared to the placebo group. Analysis of the blood indicates that the treatment patients have reduced levels of inflammatory markers, reduced gut permeability indicating an improved mucosal barrier, an increase in regulatory immune cells and a more balanced profile of metabolites from the kynurenine and serotonin pathways. The faecal analysis indicates that the treatment patients have reduced levels of bacterial overgrowth/dysbiosis and a higher level of bifidobacteria; especially members of the *Bifidobacterium adolescentis* phylogenetic group, *Bifidobacterium longum* and *Bifidobacterium bifidum*. Concentrations of short chain fatty acids are increased, and detrimental metabolites are decreased.

Example 2

A total of 272 male and female participants who suffer from recurrent migraine are recruited from the general population to participate in the study. The participants complete a baseline screening survey where they indicate any medical conditions (including migraine), and various gastrointestinal and quality of life symptoms. For the symptoms, a 5-point Likert scale is used where a score of 1 means "No symptoms" and a score of 5 means "severe symptoms". In the 272 participants, the following additional conditions are indicated:

| Condition | Number of participants |
| --- | --- |
| Irritable bowel syndrome | 86 |
| Diarrhoea | 141 |
| Constipation | 143 |
| Allergy | 137 |
| Food intolerance | 149 |
| Depression | 182 |

Each participant is provided with an amount of HMO sufficient for 3 weeks of a daily dose of about 4 g of HMO. The HMO is provided as either 2'-FL alone or a 4:1 mixture of 2'-FL and LNnT (by weight).

After 3 weeks of intake, each participant completes a second survey where they indicate various gastrointestinal and quality of life symptoms. The same 5-point Likert scale is used to assess the symptoms.

The process is repeated after 6 weeks, 9 weeks and 12 weeks.

Over the course to the 12 weeks, the headache/migraine participants indicate a reduction in headache/migraine occurrence and intensity. Further they indicate an improvement in gastrointestinal and quality of life symptoms.

Example 3

The HMOs 2'-FL and LNnT are introduced into a rotary blender in a 4:1 mass ratio. An amount of 0.25 mass % of magnesium stearate is introduced into the blender and the mixture blended for 10 minutes. The mixture is then agglomerated in a fluidised bed and filled into 5-gram stick packs and the packs sealed.

The invention claimed is:
1. A method comprising:
   selecting a non-infant patient with gastrointestinal dysbiosis and a recurrent migraine;
   selecting an effective amount of one or more human milk oligosaccharides (HMOs), for increasing a relative abundance of *Bifidobacterium adolescentis* in the gastrointestinal microbiota of the non-infant patient;

modulating the gastrointestinal microbiota of the non-infant patient by administering the selected effective amount of the one or more HMOs; and reducing frequency and/or severity of the recurrent migraine.

2. The method of claim 1, wherein the non-infant patient has irritable bowel syndrome.

3. The method of claim 1, wherein modulating the gastrointestinal microbiota of the non-infant patient comprises increasing the relative abundance of *Bifidobacterium adolescentis* in the gastrointestinal microbiota of the non-infant patient by administering the selected effective amount of the one or more HMOs.

4. The method of claim 1, wherein the one or more HMOs are selected from 2'-fucosyllactose ("2'FL"), 3-fucosyllactose ("3FL"), difucosyllactose ("DFL"), lacto-N-fucopentaose ("LNFP-1"), lacto-N-neotetraose ("LNnT"), lacto-N-tetraose ("LNT"), 3'-sialyllactose ("3'SL"), 6'-sialyllactose ("6'SL"), and mixtures thereof.

5. The method of claim 1, wherein modulating the gastrointestinal microbiota of the non-infant human comprises increasing the relative abundance of *Faecalibacterium*.

6. The method of claim 1, wherein modulating the gastrointestinal microbiota of the non-infant human further comprises reducing the relative abundance of Proteobacteria.

7. The method of claim 1, further comprising improving mucosal barrier function in the gastrointestinal tract of the non-infant patient by administering the selected effective amount of the one or more HMOs.

8. The method of claim 1, further comprising reducing a serum level of one more inflammatory markers by administering to the non-infant patient the selected effective amount of the one or more HMOs.

9. A method comprising:
selecting a non-infant female human with recurrent migraine;
selecting an effective amount of one or more human milk oligosaccharides ("HMOs") for reducing recurrent migraine; and
reducing frequency and/or severity of recurrent migraine experienced by the non-infant female human by administering the selected effective amount of the one or more HMOs.

10. The method of claim 9 wherein the non-infant human is administered an amount of 1 g to 15 g per day of the human milk oligosaccharide.

11. The method of claim 9, in which the non-infant human is administered the human milk oligosaccharide for a period of at least 1 week.

12. The method of claim 9, wherein the non-infant human has a condition with gastrointestinal symptoms.

13. The method of claim 12, in which the condition is an autoimmune disease, irritable bowel syndrome, an allergy, and/or a food intolerance.

14. The method of claim 9, wherein the one or more HMOs are selected from 2'-fucosyllactose ("2'FL"), 3-fucosyllactose ("3FL"), difucosyllactose ("DFL"), lacto-N-fucopentaose ("LNFP-1"), lacto-N-neotetraose ("LNnT"), lacto-N-tetraose ("LNT"), 3'sialyllactose ("3'SL"), 6'-sialyllactose ("6'SL"), and mixtures thereof.

15. The method of claim 9, wherein the one or more HMOs consisting essentially of a mixture of a fucosylated HMO and a non-fucosylated neutral HMO.

16. The method of claim 15, wherein:
the fucosylated HMO is selected from 2'FL, DFL, and a mixture thereof; and
the non-fucosylated neutral HMO is selected from LNnT, LNT, and a mixture thereof.

17. The method of claim 15, wherein the one or more HMOs consists essentially of a mixture of 2'FL and LNnT in a mass ratio of from about 4:1 to about 1:1.

18. The method of claim 9, wherein a first dosage is selected as the effective amount of the one or more HMOs administered to the non-infant human during an initial treatment phase is higher than a second dosage selected as the effective amount of the one or more HMOs administered during a maintenance phase.

19. The method of claim 18, wherein the first dosage administered during the initial treatment phase is from 3 g to 15 g per day, and the second dosage administered during the maintenance phase is from 2 g to 7.5 g per day.

20. A method comprising:
selecting a chronic migraine patient that is a non-infant;
selecting an effective amount of one or more human milk oligosaccharides ("HMOs") for reducing an average number of headache days and/or the severity of migraine symptoms experienced by the chronic migraine patient; and
reducing the average number of headache days and/or the severity of migraine symptoms experienced by the chronic migraine patient by administering to the chronic migraine patient the selected effective amount of the one or more HMOs for a period of at least 14 days.

* * * * *